(12) United States Patent
Janssen et al.

(10) Patent No.: US 6,537,941 B2
(45) Date of Patent: Mar. 25, 2003

(54) REJUVENATING SAPO MOLECULAR SIEVE BY FREEZE DRYING

(75) Inventors: Marcel J. G. Janssen, Kessel Lo (BE); Cornelis W. M. Van Oorschot, Brasschaat (BE); Kenneth R. Clem, Humble, TX (US)

(73) Assignee: ExxonMobil Chemical Patents, Inc., Houston, TX (US)

( * ) Notice: Subject to any disclaimer, the term of this patent is extended or adjusted under 35 U.S.C. 154(b) by 0 days.

(21) Appl. No.: 09/754,812

(22) Filed: Jan. 4, 2001

(65) Prior Publication Data

US 2002/0115897 A1 Aug. 22, 2002

(51) Int. Cl.$^7$ .................................................. B01J 23/90
(52) U.S. Cl. ........................ 502/20; 502/208; 502/214
(58) Field of Search ........................... 502/20, 206, 214

(56) References Cited

U.S. PATENT DOCUMENTS

| 4,681,864 A | 7/1987 | Edwards et al. |
| 4,842,714 A | 6/1989 | Pellet et al. |
| 5,185,310 A | 2/1993 | Degnan et al. |
| 5,248,647 A | 9/1993 | Barger |
| 5,744,680 A | 4/1998 | Mulvaney, III et al. |

FOREIGN PATENT DOCUMENTS

| DE | 3627468 | 5/1987 | ......... F26B/005/06 |
| EP | 0 163 560 | 10/1985 | ............. C01B/3/26 |
| EP | 1 184 449 | 4/2000 | ............ C11D/3/37 |
| WO | WO 94/05597 | 3/1994 | .......... C01B/33/26 |

OTHER PUBLICATIONS

Wilson et al., "The Characteristics if SAPO–34 which influence the Conversion of Methanol to Light Olefins", *Microporous and Mesoporous Materials*, vol. 29, pp. 117–126 Elsevier (1999).

Gabelica et al. "Novel approach to the Synthesis of Molecular Sieves. Recrystallization of the Intermediates Isolated from the Gel Phase", *Symposium on Advances in Zeolites and Pillared Clay Synthesis*; New York; NY, vol. 36, No. 2, p. 367 (Jul. 1991).

*Primary Examiner*—Stanley S. Silverman
*Assistant Examiner*—Edward M. Johnson

(57) ABSTRACT

The method includes freeze drying a molecular sieve having a methanol conversion ratio of less than 1, or a catalyst containing molecular sieve and a binder having a methanol conversion ratio of less than 1. The rejuvenated molecular sieve or catalyst is used to make an olefin product from an oxygenate. The olefin product containing ethylene and propylene can then be used to make polyethylene and polypropylene, respectively.

16 Claims, 1 Drawing Sheet

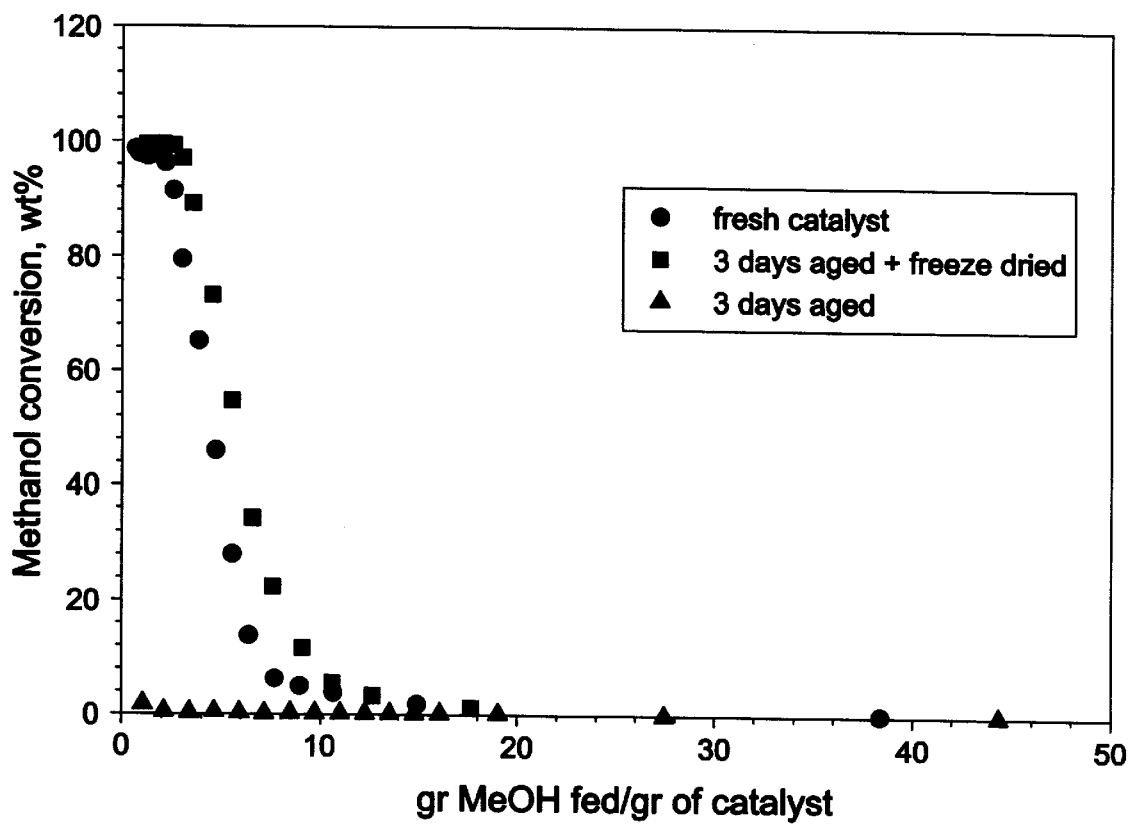

REJUVENATING SAPO MOLECULAR SIEVE BY FREEZE DRYING

FIELD OF THE INVENTION

This invention is directed to a method of rejuvenating molecular sieve or catalyst containing molecular sieve, and a method of using the rejuvenated molecular sieve or catalyst to make an olefin product from methanol. In particular, the invention is directed to rejuvenating a silicoaluminophosphate (SAPO) molecular sieve or SAPO catalyst by freeze drying the molecular sieve or catalyst prior to converting the methanol feed.

BACKGROUND OF THE INVENTION

Silicoaluminophosphates (SAPOs) have been used as adsorbents and catalysts. As catalysts, SAPOs have been used in processes such as fluid catalytic cracking, hydrocracking, isomerization, oligomerization, the conversion of alcohols or ethers, and the alkylation of aromatics. In particular, the use of SAPOs in converting alcohols or ethers to olefin products, particularly ethylene and propylene, is becoming of greater interest for large scale, commercial production facilities.

As is known in the development of new large scale, commercial production facilities in the commodity chemical business, many problems arise in the scale up from laboratory and pilot plant operations. Scale up problems arise in catalytic reaction systems in which large scale operation will be several orders of magnitude larger than typical pilot scale facilities. For example, conventional laboratory scale processes of making olefin products from oxygenate feed are conducted with catalyst loads of about 0.1 to 5 grams. Conventional large pilot plant operations may utilize as much as 50 kg of catalyst, making on the order of 20 kg/hr ethylene and propylene product, but this is nevertheless minuscule in comparison to what a large scale, commercial production facility would produce, if one were in existence today. Large scale, commercial production facilities, can require a catalyst loading of anywhere from 1,000 kg to 700,000 kg, producing anywhere from 600 to 400,000 kg/hr of ethylene and propylene product.

Operating large scale, commercial production facilities clearly presents great challenges in the development of the catalyst production-to-use chain. The term "production-to-use chain" refers to the entire area of activities beginning with the production of molecular sieve, including such activities as receipt of starting materials, on through the crystallization process. Also included in the production-to-use chain are intermediate activities which include formulation of the sieve with binders and other materials, activation of the manufactured sieve and finished catalyst; storage, transport, loading, unloading of molecular sieve and finished catalyst; as well as other practices associated with the handling and preparation of the sieve and finished catalyst for its ultimate use. The production-to-use chain ends at the point when the molecular sieve is introduced into the reaction system. For purposes of this invention, the end of the production-to-use chain does not necessarily mean the instant when the molecular sieve is introduced into the reaction system, since large scale systems are very large and instantaneous measurements are not practically feasible. In large scale systems, the production-to-use chain may be considered as completed some time within 12 hours of loading catalyst into the reaction system.

Since information to date relating to production of olefin products by catalytic conversion of oxygenate feedstock has been limited to laboratory and small pilot plant activities, little if any attention has been paid to the problems associated with the intermediate activities in the production-to-use chain. For example, little attention has been focused on the impact of storage, transport, etc. on catalyst activity, since small scale activity is rather easily manageable. While today only relatively small quantities of catalyst are prepared, stored and transported, large quantities of materials will need to be handled for commercial operations. Commercial operations may be require that large quantities of molecular sieve catalysts be stored for considerable periods of time and at multiple locations.

As the management of sieve and catalyst in the catalyst production-to-use chain expands in volume and complexity, a likelihood exists that millions of dollars will be tied up in catalyst inventory, and the value of the sieve and catalyst will be lost if quality, as compared to that of freshly prepared and calcined catalyst, is not maintained. Loss of quality will necessarily translate to loss of product quality, as well as loss of product quantity.

Although some work has been published relating to the intermediate activities in the catalyst production-to-use chain, few of the problems associated therewith have been addressed. For example, U.S. Pat. No. 4,681,864 to Edwards et al. discuss the use of SAPO-37 molecular sieve as a commercial cracking catalyst. It is disclosed that activated SAPO-37 molecular sieve has poor stability, and that stability can be improved by using a particular activation process. In this process, organic template is removed from the core structure of the sieve just prior to contacting with feed to be cracked. The process calls for subjecting the sieve to a temperature of 400–800° C. within the catalytic cracking unit.

U.S. Pat. No. 5,185,310 to Degnan et al. discloses a particular method of calcining SAPO catalyst containing alumina as a binder. The method calls for heating the catalyst to at least 425° C. in the presence of an oxygen depleted gas, and then in the presence of an oxidizing gas. The object of the heating process is to maintain the acid activity of the catalyst.

Briend et al., *J. Phys. Chem.* 1995, 99, 8270–8276, teach that SAPO-34 loses its crystallinity when the template has been removed from the sieve and the de-templated, activated sieve has been exposed to air. Data is presented, however, which suggests that over at least the short term, this crystallinity loss is reversible. Even over a period of perhaps two years, the data suggest that crystallinity loss is reversible when certain templates are used.

EP-A2-0 203 005 also discusses the use of SAPO-37 molecular sieve in a zeolite catalyst composite as a commercial cracking catalyst. According to the document, if the organic template is retained in the SAPO-37 molecular sieve until a catalyst composite containing zeolite and the SAPO-37 molecular sieve is activated during use, and if thereafter the catalyst is maintained under conditions wherein exposure to moisture is minimized, the crystalline structure of the SAPO-37 zeolite composite remains stable.

Researchers at ExxonMobil Chemical Company has recently discovered that activated SAPO molecular sieve will exhibit a loss of catalytic activity when exposed to a moisture-containing environment. This loss of activity can occur between the time the catalyst is activated and even after as little as one day of storage. Although ways have been found to inhibit loss of catalytic activity, it would be highly beneficial to find a way to reverse the decrease of catalytic activity in a molecular sieve exposed to a moisture-containing environment.

SUMMARY OF THE INVENTION

In order to overcome the various problems associated with decrease of activity of a molecular sieve due to contact by moisture, this invention provides a way to reverse such decrease, i.e., to rejuvenate the molecular sieve. In general, this invention provides a process for rejuvenating a molecular sieve which comprises providing molecular sieve having a methanol uptake index of less than 1; and freeze drying the molecular sieve until the methanol uptake index is increased by at least 10%.

Preferably, the methanol uptake index is increased by at least 50%, more preferably the methanol uptake index is increased by at least 100%, and most preferably the methanol uptake index is increased by at least 500%. It is also preferred that the molecular sieve be provided having a methanol uptake index of less than 0.5, more preferably a methanol uptake index of less than 0.3, and most preferably, a methanol uptake index of less than 0.15.

Desirably, the molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO41, SAPO-42, SAPO-44, SAPO-47, SAPO-56, ALPO-5, ALPO-11, ALPO-18, ALPO-31, ALPO-34, ALPO-36, ALPO-37, ALPO46, the metal containing forms of each thereof, and mixtures thereof Preferably, the molecular sieve is selected from the group consisting of SAPO-17, SAPO-18, SAPO-34, SAPO-35, SAPO-44, SAPO-47, the metal containing forms of each thereof, and mixtures thereof.

In a preferred embodiment, freeze drying is carried out at a pressure of 0.001 mtorr to 700 torr. Preferably, freeze drying is also carried out at a temperature of −200° C. to 0° C.

The invention also provides a method for rejuvenating molecular sieve containing catalyst which comprises providing molecular sieve containing catalyst having a methanol uptake index of less than 1; and freeze drying the molecular sieve containing catalyst until the methanol uptake index is increased by at least 10%.

The invention is further to a method of making an olefin product from an oxygenate which comprises providing molecular sieve containing catalyst having a methanol uptake index of less than 1; freeze drying the molecular sieve containing catalyst until the methanol uptake index is increased by at least 10%; and contacting the freeze dried molecular sieve containing catalyst with an oxygenate to produce olefin product. In a preferred embodiment, the freeze dried molecular sieve containing catalyst is contacted with an oxygenate at a temperature of 200° C. to 700° C. Preferably, the olefin product comprises ethylene and propylene. Desirably, the ethylene and propylene are separated into at least two product streams. The separated ethylene and propylene can then be contacted with a polyolefin-forming catalyst to form polyethylene and polypropylene.

The invention will be better understood by reference to the Detailed Description of the Invention when taken together with the attached FIGURE and in association with the appended claims.

BRIEF DESCRIPTION OF THE DRAWINGS

The FIGURE shows methanol conversion for fresh, rejuvenated, and moisture aged SAPO molecular sieve.

DETAILED DESCRIPTION OF THE INVENTION

Silicoaluminophosphate (SAPO) molecular sieves, in particular, are susceptible to structural changes as a result of continued exposure to even low levels of moisture. Such authorities as Paulitz et al., *Microporous Materials*, 2, 223–228 (1994), however, have shown through X-ray diffraction (XRD), nuclear magnetic resonance (NMR), infrared (IR) and nitrogen ($N_2$) adsorption analyses that the structural change is largely reversible. These X-ray diffraction studies have, nevertheless, been found to be unreliable in determining loss of catalytic activity of these sieves. For example, Paulitz et al. have shown that SAPO molecular sieve once structurally altered by contact with moisture can be rejuvenated by calcination to exhibit its typical X-ray diffraction pattern. However, the same procedure has been shown not to rejuvenate catalytic activity of the molecular sieve. See, for example, U.S. Ser. No. 09/391,770 to ExxonMobil Chemical Company.

The loss of catalytic activity as a result of contact of molecular sieve with moisture presents a problem in the commercial production-to-use chain where storage and transport of molecular sieve and catalyst can occupy relatively long periods of time. For example, it is possible that molecular sieve or catalyst containing molecular sieve can be stored from 12 hours to many months, perhaps as long as one year before its use in a catalytic process. This stored sieve or catalyst is likely not to have a template within its internal pore structure as a result of having been removed by calcination prior to storage. Such a sieve or catalyst would be especially susceptible to damage by contact with moisture. Even partial loss of catalytic activity is of particular concern in a large scale catalytic process. As defined herein, a large scale catalytic process is one having a reactor loading in excess of 50 kg, particularly one having a reactor system loading in excess of 500 kg, especially one having a reactor loading in excess of 5000 kg.

The term "catalytic activity" used herein refers to the conversion of oxygenate to total product, including olefin, based upon the grams of methanol converted per gram of molecular sieve for a given space velocity (residence time). Therefore, molecular sieve having a higher conversion to total product (less oxygenate in the product) for a given space velocity will have a greater catalytic activity, regardless of the product selectivity. In the case of molecular sieve catalyst, the weight of the molecular sieve in the catalyst is used to determine catalytic activity.

SAPO molecular sieve, as well as catalyst containing SAPO molecular sieve, which exhibits decreased catalytic activity as a result of contact with moisture can be rejuvenated by freeze drying. The term freeze drying as used herein describes a process in which a solid or a slurry containing a solid is placed within a container and cooled or frozen under vacuum. The container is connected to one or more vacuum sources, and a vacuum (pressure less than 760 torr) is applied. The container is then cooled to a temperature less than 0° C., preferably between −200° C. and 0° C. One method of cooling the container, which in turn cools the material in the container, may include placing the container in a liquid or gas coolant. Coolants that may be used include liquid nitrogen, liquid or solid carbon dioxide, organic refrigerants, e.g., fluorocarbon refrigerants. Water and/or other volatile components which may be present within the sieve or catalyst will typically be removed as a result of applying the vacuum conditions. The water, or other volatile material which may be present, is then removed from the container by way of the vacuum source.

In one embodiment, a molecular sieve or molecular sieve catalyst that has been exposed to a moisture containing environment is added to a container. A vacuum pump connected to the container creates a vacuum in the container, i.e., a pressure of less than 760 torr. Preferably, the pressure is between 0.001 mtorr and 700 torr, more preferably between 0.01 mtorr and 4 torr, and most preferably between 0.02 mtorr and 0.1 torr. The sieve or catalyst is also cooled to a temperature between −200° C. and 0° C., preferably between −175° C. and −25° C., more preferably between −150° C. and −50° C.

The sieve or catalyst is cooled under vacuum until the sieve or catalyst has an increase in catalytic activity. Preferably, the vacuum is removed and the sieve or catalyst is allowed to warm. Heat can be applied if desired. Preferably, the sieve or catalyst is heated to a temperature between 10° C. and 200° C., more preferably, between 20° C. and 100° C. Gas, e.g., air, that may be introduced to the container following removal of the vacuum is preferably low in moisture content. Preferably, the introduced gas will contain less than about 100 ppm water, more preferably less than about 50 ppm water, and most preferably less than about 10 ppm water.

The freeze dried sieve or catalyst can then be transferred to a reactor, heated to a temperature between 400° C. and 800° C., preferably between 450° C. and 700° C. Preferably, heating is carried out under inert atmosphere, e.g., nitrogen, helium, etc., for about 1 hour. Alternatively, an oxidizing atmosphere can be used, e.g., air. The temperature of the reactor is desirably set to a temperature that is optimized for the conversion of an oxygenate to an olefin. Methanol is introduced to the reactor and the products from the conversion of methanol determined.

It is to be understood in this invention that the freeze drying process can be carried out in the reactor. As a result, the molecular sieve or catalyst does not have to be transferred to another container. Also, both the freeze drying process and the heating can be carried out in one or more units separate from the reactor. For example, a freeze drying unit can be connected to a heating unit which feeds the reactor with catalyst. A freeze drying unit is the equipment used in the freeze drying process. The freeze drying unit includes a container to contain the sieve or catalyst, one or more evacuation ports, and a coolant system.

SAPO molecular sieve, as well as catalyst containing SAPO molecular sieve, which exhibits decreased catalytic activity as a result of contact with moisture can be rejuvenated by freeze drying the sieve or catalyst. According to this invention, rejuvenation of a molecular sieve is determined using a methanol uptake index. A molecular sieve having a methanol uptake index of less than 1 is capable of being rejuvenated.

As used herein, methanol uptake index is defined as the methanol adsorption capacity (wt. %) of a microporous SAPO molecular sieve having been exposed to moisture, divided by the maximum methanol adsorption capacity (wt. %) of a non-moisture exposed SAPO molecular sieve (i.e., the initial or maximum methanol adsorption capacity of a fresh, non-moisture exposed sieve). Techniques for measuring methanol adsorption capacity are known to those of ordinary skill in the art. In a preferred technique, about 5 mg of sample is introduced into a thermogravimetric analyzer (TGA). The sample is subjected to a heat treatment process, which includes: (1) heating from room temperature to 450° C., with a heat up rate of 20° C./min. in air; (2) holding at 450° C. for 40 min. in air; and cooling to 30° C. in air. After the sample has reached 30° C., the air flow in the TGA is switched to a methanol containing nitrogen flow with a methanol partial pressure of 0.09 atm. The sample is contacted with this nitrogen/methanol mixture for 180 minutes. The methanol adsorption capacity is the weight percent weight increase after the 180 minutes contact with the methanol vapor.

In this invention, rejuvenation is considered to be demonstrated when the rejuvenation process results in a relative increase in the methanol uptake index of at least about 10%. Preferably, the rejuvenation process will result in an increase in the methanol uptake index of at least about 50%, more preferably at least about 100%, and most preferably at least about 500%, the increase being calculated as the change before rejuvenation and after rejuvenation on a percent basis.

The lower the methanol uptake index of a moisture exposed molecular sieve, the more suitable the molecular sieve for rejuvenation. From an efficiency standpoint, it is desirable to rejuvenate a molecular sieve which has a methanol uptake index of less than about 0.5, preferably less than about 0.3, more preferably less than about 0.2, and most preferably less than about 0.15. Complete rejuvenation results in a methanol uptake index of 1.

It is also preferred in this invention that the freeze drying rejuvenation process be carried out until a methanol uptake index of at least 0.4 is achieved, preferably until a methanol uptake index of at least 0.6 is achieved, more preferably until a methanol uptake index of at least 0.7 is achieved, and most preferably until a methanol uptake index of at least 0.8 is achieved. Thus, in the more-practical form of this invention, a molecular sieve having a methanol uptake index of less than about 0.4 is a more likely candidate for rejuvenation, although a molecular sieve having a methanol uptake index of less than 1 is capable of being rejuvenated. It is preferred that rejuvenation, or freeze drying, be carried out until a methanol uptake index of at least 0.4 is achieved so that the sieve will of benefit in a commercial scale system. Anything below 0.4 means that the catalytic activity of the sieve would be less than 40%, which is extremely low for a commercial process.

The catalyst that is used in this invention is one that incorporates a silicoaluminophosphate (SAPO) molecular sieve. The molecular sieve comprises a three-dimensional microporous crystal framework structure of [$SiO_2$], [$AlO_2$] and [$PO_2$] tetrahedral units. The way Si is incorporated into the structure can be determined by $^{29}$Si MAS NMR. See Blackwell and Patton, *J Phys. Chem.*, 92, 3965 (1988). The desired SAPO molecular sieves will exhibit one or more peaks in the $^{29}$Si MAS NMR, with a chemical shift δ (Si) in the range of −88 to −96 ppm and with a combined peak area in that range of at least 20% of the total peak area of all peaks with a chemical shift δ (Si) of −88 ppm to −115 ppm, when the δ (Si) chemical shifts refer to external tetramethylsilane (TMS).

It is preferred that the silicoaluminophosphate molecular sieve used in this invention have a relatively low Si/$Al_2$ ratio. In general, the lower the Si/Al2 ratio, the lower the $C_1$–$C_4$ saturates selectivity, particularly propane selectivity. A Si/Al2 ratio of less than 0.65 is desirable, with a Si/$Al_2$ ratio of not greater than 0.40 being preferred, and a Si/$Al_2$ ratio of not greater than 0.32 being particularly preferred. A Si/$Al_2$ ratio of not greater than 0.20 is most preferred.

Silicoaluminophosphate molecular sieves are generally classified as being microporous materials having 8, 10, or 12 membered ring structures. These ring structures can have an average pore size of about 3.5 angstroms to about 15 angstroms. Preferred are the small pore SAPO molecular sieves having an average pore size of less than about 5 angstroms, preferably an average pore size of 3.5 angstroms to 5 angstroms, more preferably from 3.5 angstroms to 4.2 angstroms. These pore sizes are typical of molecular sieves having 8 membered rings.

In general, silicoaluminophosphate molecular sieves comprise a molecular framework of corner-sharing [$SiO_2$], [$AlO_2$], and [$PO_2$] tetrahedral units. This type of framework is effective in converting various oxygenates into olefin products.

The [$PO_2$] tetrahedral units within the framework structure of the molecular sieve of this invention can be provided by a variety of compositions. Examples of these phosphorus-containing compositions include phosphoric acid, organic phosphates such as triethyl phosphate, and aluminophosphates. The phosphorous-containing compositions are mixed with reactive silicon and aluminum-containing compositions under the appropriate conditions to form the molecular sieve.

The [$AlO_2$] tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The [$SiO_2$] tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphorus-containing compositions under the appropriate conditions to form the molecular sieve.

Substituted SAPOs can also be used in this invention. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium, and scandium or yttrium) and the additional transition cations of Groups IVB, VB, VIB, VIIB, VIIIB, IB, and IIB.

Preferably, the Me represents atoms such as Zn, Mg, Mn, Co, Ni, Ga, Fe, Ti, Zr, Ge, Sn, and Cr. These atoms can be inserted into the tetrahedral framework through a [$MeO_2$] tetrahedral unit. The [$MeO_2$] tetrahedral unit carries a net electric charge depending on the valence state of the metal substituent. When the metal component has a valence state of +2, +3, +4, +5, or +6, the net electric charge is between −2 and +2. Incorporation of the metal component is typically accomplished adding the metal component during synthesis of the molecular sieve. However, post-synthesis ion exchange can also be used.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof Preferred are SAPO-17, SAPO-18, SAPO-34, SAPO-35, SAPO44, and SAPO-47, particularly SAPO-18 and SAPO-34, including the metal containing forms thereof, and mixtures thereof As used herein, the term mixture is synonymous with combination and is considered a composition of matter having two or more components in varying proportions, regardless of their physical state.

An aluminophosphate (ALPO) molecular sieve can also be included in the catalyst composition. Aluminophosphate molecular sieves are crystalline microporous oxides which can have an $AlPO_4$ framework. They can have additional elements within the framework, typically have uniform pore dimensions of about 3 angstroms to about 10angstroms, and are capable of making size selective separations of molecular species. More than two dozen structure types have been reported, including zeolite topological analogues. A more detailed description of the background and synthesis of aluminophosphates is found in U.S. Pat. No. 4,310,440, which is incorporated herein by reference in its entirety. Preferred ALPO structures are ALPO-5, ALPO-11, ALPO-18, ALPO-3 1, ALPO-34, ALPO-36, ALPO-37, and ALPO-46.

The ALPOs can also include a metal substituent in its framework. Preferably, the metal is selected from the group consisting of magnesium, manganese, zinc, cobalt, and mixtures thereof. These materials preferably exhibit adsorption, ion-exchange and/or catalytic properties similar to aluminosilicate, aluminophosphate and silica aluminophosphate molecular sieve compositions. Members of this class and their preparation are described in U.S. Pat. No. 4,567,029, incorporated herein by reference in its entirety.

The metal containing ALPOs have a three-dimensional microporous crystal framework structure of $MO_2$, $AMO_2$ and $PO_2$ tetrahedral units. These as manufactured structures (which contain template prior to calcination) can be represented by empirical chemical composition, on an anhydrous basis, as:

$$mR: (M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved, "x", "y", and "z" represent the mole fractions of the metal "M", (i.e. magnesium, manganese, zinc and cobalt), aluminum and phosphorus, respectively, present as tetrahedral oxides.

The metal containing ALPOs are sometimes referred to by the acronym as MeAPO. Also in those cases where the metal "Me" in the composition is magnesium, the acronym MAPO is applied to the composition. Similarly ZAPO, MnAPO and CoAPO are applied to the compositions which contain zinc, manganese and cobalt respectively. To identify the various structural species which make up each of the subgeneric classes MAPO, ZAPO, CoAPO and MnAPO, each species is assigned a number and is identified, for example, as ZAPO-5, MAPO-11, CoAPO-34 and so forth.

The silicoaluminophosphate molecular sieves are synthesized by hydrothermal crystallization methods generally known in the art. See, for example, U.S. Pat. Nos. 4,440,871; 4,861,743; 5,096,684; and 5,126,308, the methods of making of which are fully incorporated herein by reference. A reaction mixture is formed by mixing together reactive silicon, aluminum and phosphorus components, along with at least one template. Generally the mixture is sealed and heated, preferably under autogenous pressure, to a temperature of at least 100° C., preferably from 100° C. to 250° C., until a crystalline product is formed. Formation of the crystalline product can take anywhere from around 2 hours to as much as 2 weeks. In some cases, stirring or seeding with crystalline material will facilitate the formation of the product.

Typically, the molecular sieve product will be formed in solution. It can be recovered by standard means, such as by centrifugation or filtration. The product can also be washed, recovered by the same means and dried.

As a result of the crystallization process, the recovered sieve contains within its pores at least a portion of the template used in making the initial reaction mixture. The crystalline structure essentially wraps around the template, and the template must be removed so that the molecular sieve can exhibit catalytic activity. Once the template is removed, the crystalline structure that remains has what is typically called an intracrystalline pore system.

In many cases, depending upon the nature of the final product formed, the template may be too large to be eluted from the intracrystalline pore system. In such a case, the template can be removed by a heat treatment process. For example, the template can be calcined, or essentially combusted, in the presence of an oxygen-containing gas, by contacting the template-containing sieve in the presence of the oxygen-containing gas and heating at temperatures from 200° C. to 900° C. In some cases, it may be desirable to heat in an environment having a low oxygen concentration. In these cases, however, the result will typically be a breakdown of the template into a smaller component, rather than by the combustion process. This type of process can be used for partial or complete removal of the template from the intracrystalline pore system. In other cases, with smaller templates, complete or partial removal from the sieve can be accomplished by conventional desorption processes such as those used in making standard zeolites.

The reaction mixture can contain one or more templates. Templates are structure directing agents, and typically contain nitrogen, phosphorus, oxygen, carbon, hydrogen or a combination thereof, and can also contain at least one alkyl or aryl group, with 1 to 8 carbons being present in the alkyl or aryl group. Mixtures of two or more templates can produce mixtures of different sieves or predominantly one sieve where one template is more strongly directing than another.

Representative templates include tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine and combinations thereof Preferred templates are triethylamine, cyclohexylamine, piperidine, pyridine, isopropylamine, tetraethyl ammonium salts, dipropylamine, and mixtures thereof. The tetraethylammonium salts include tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Preferred tetraethyl ammonium salts are tetraethyl ammonium hydroxide and tetraethyl ammonium phosphate.

The SAPO molecular sieve structure can be effectively controlled using combinations of templates. For example, in a particularly preferred embodiment, the SAPO molecular sieve is manufactured using a template combination of TEAOH and dipropylamine. This combination results in a particularly desirable SAPO structure for the conversion of oxygenates, particularly methanol and dimethyl ether, to light olefins such as ethylene and propylene.

The silicoaluminophosphate molecular sieve is typically admixed (i.e., blended) with other materials. When blended, the resulting composition is typically referred to as a SAPO catalyst, with the catalyst comprising the SAPO molecular sieve.

Materials which can be blended with the molecular sieve can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, quartz, silica or silica or silica sol, and mixtures thereof. These components are also effective in reducing, inter alia, overall catalyst cost, acting as a thermal sink to assist in heat shielding the catalyst during regeneration, densifying the catalyst and increasing catalyst strength. It is particularly desirable that the inert materials that are used in the catalyst to act as a thermal sink have a heat capacity of from about 0.05 cal/g-° C. to about 1 cal/g-° C., more preferably from about 0.1 cal/g-° C. to about 0.8 cal/g-° C., most preferably from about 0.1 cat/g-° C. to about 0.5 cal/g-° C.

Additional molecular sieve materials can be included as a part of the SAPO catalyst composition or they can be used as separate molecular sieve catalysts in admixture with the SAPO catalyst if desired. Structural types of small pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted for ms thereof Structural types of medium pore molecular sieves that are suitable for use in this invention include MFI, MEL, MTW, EUO, MTT, HEU, FER, AFO, AEL, TON, and substituted forms thereof. Preferred molecular sieves which can be combined with a silicoaluminophosphate catalyst include ZSM-5, ZSM-34, erionite, and chabazite.

The catalyst composition preferably comprises about 1% to about 99 %, more preferably about 5 % to about 90 %, and most preferably about 10% to about 80%, by weight of molecular sieve. It is also preferred that the catalyst composition have a particle size of from about 20 $\mu$m to 3,000 $\mu$m, more preferably about 30$\mu$m to 200$\mu$m, most preferably about 50 $\mu$m to 150 $\mu$m.

The catalyst can be subjected to a variety of treatments to achieve the desired physical and chemical characteristics. Such treatments include, but are not necessarily limited to hydrothermal treatment, calcination, acid treatment, base treatment, milling, ball milling, grinding, spray drying, and combinations thereof.

It is particularly desirable that the rejuvenated molecular sieve of this invention be used in the process of making olefin product from an oxygenate-containing feedstock. In one embodiment of this invention, a feed containing an oxygenate, and optionally a diluent or a hydrocarbon added separately or mixed with the oxygenate, is contacted with a catalyst containing a rejuvenated SAPO molecular sieve in a reaction zone or volume. The volume in which such contact takes place is herein termed the "reactor," which may be a part of a "reactor apparatus" or "reaction system." Another part of the reaction system may be a "regenerator," which comprises a volume wherein carbonaceous deposits (or coke) on the catalyst resulting from the olefin conversion reaction are removed by contacting the catalyst with regeneration medium.

The oxygenate feedstock of this invention comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts.

Examples of suitable oxygenate compounds include, but are not limited to: methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof The method of making the preferred olefin product in this invention can include the additional step of making these compositions from hydrocarbons such as oil, coal, tar sand, shale, biomass and natural gas. Methods for making the compositions are known in the art. These methods include fermentation to alcohol or ether, making synthesis gas, then converting the synthesis gas to alcohol or ether. Synthesis gas can be produced by known processes such as steam reforming, autothermal reforming and partial oxidization.

One or more inert diluents may be present in the feedstock, for example, in an amount of from 1 to 99 molar percent, based on the total number of moles of all feed and diluent components fed to the reaction zone (or catalyst). As defined herein, diluents are compositions which are essentially non-reactive across a molecular sieve catalyst, and primarily function to make the oxygenates in the feedstock less concentrated. Typical diluents include, but are not necessarily limited to helium, argon, nitrogen, carbon monoxide, carbon dioxide, water, essentially non-reactive paraffins (especially the alkanes such as methane, ethane, and propane), essentially non-reactive alkylenes, essentially non-reactive aromatic compounds, and mixtures thereof The preferred diluents are water and nitrogen. Water can be injected in either liquid or vapor form.

Hydrocarbons can also be included as part of the feedstock, i.e., as co-feed. As defined herein, hydrocarbons included with the feedstock are hydrocarbon compositions which are converted to another chemical arrangement when contacted with molecular sieve catalyst. These hydrocarbons can include olefins, reactive paraffins, reactive alkylaromatics, reactive aromatics or mixtures thereof. Preferred hydrocarbon co-feeds include, propylene, butylene, pentylene, $C_4^+$ hydrocarbon mixtures, $C_5^+$ hydrocarbon mixtures, and mixtures thereof. More preferred as co-feeds are a $C_4^+$ hydrocarbon mixtures, with the most preferred being $C_4^+$ hydrocarbon mixtures which are obtained from separation and recycle of reactor product.

In the process of this invention, coked catalyst can be regenerated by contacting the coked catalyst with a regeneration medium to remove all or part of the coke deposits. This regeneration can occur periodically within the reactor by ceasing the flow of feed to the reactor, introducing a regeneration medium, ceasing flow of the regeneration medium, and then reintroducing the feed to the fully or partially regenerated catalyst. Regeneration may also occur periodically or continuously outside the reactor by removing a portion of the deactivated catalyst to a separate regenerator, regenerating the coked catalyst in the regenerator, and subsequently reintroducing the regenerated catalyst to the reactor. Regeneration can occur at times and conditions appropriate to maintain a desired level of coke on the entire catalyst within the reactor.

Catalyst that has been contacted with feed in a reactor is defined herein as "feedstock exposed." Feedstock exposed catalyst will provide olefin conversion reaction products having substantially lower propane and coke content than a catalyst which is fresh and regenerated. A catalyst will typically provide lower amounts of propane as it is exposed to more feed, either through increasing time at a given feed rate or increasing feed rate over a given time.

At any given instant in time, some of the catalyst in the reactor will be fresh, some regenerated, and some coked or partially coked as a result of having not yet been regenerated. Therefore, various portions of the catalyst in the reactor will have been feedstock exposed for different periods of time. Since the rate at which feed flows to the reactor can vary, the amount of feed to which various portions of the catalyst can also vary. To account for this variation, the "average catalyst feedstock exposure index (ACFE index)" is used to quantitatively define the extent to which the entire catalyst in the reactor has been feedstock exposed.

As used herein, ACFE index is the total weight of feed divided by the total weight of molecular sieve (i.e., excluding binder, inerts, etc., of the catalyst composition) sent to the reactor. The measurement should be made over an equivalent time interval, and the time interval should be long enough to smooth out fluctuations in catalyst or feedstock rates according to the reactor and regeneration process step selected to allow the system to be viewed as essentially continuous. In the case of reactor systems with periodic regenerations, this can range from hours up to days or longer. In the case of reactor systems with substantially constant regeneration, minutes or hours may be sufficient.

Flow rate of catalyst can be measured in a variety of ways. In the design of the equipment used to carry the catalyst between the reactor and regenerator, the catalyst flow rate can be determined given the coke production rate in the reactor, the average coke level on catalyst leaving the reactor, and the average coke level on catalyst leaving the regenerator. In an operating unit with continuous catalyst flow, a variety of measurement techniques can be used. Many such techniques are described, for example, by Michel Louge, "Experimental Techniques," *Circulating Fluidized Beds*, Grace, Avidan, & Knowlton, eds., Blackie, 1997 (336–337), the descriptions of which are expressly incorporated herein by reference.

In this invention, only the molecular sieve in the catalyst sent to the reactor may be used in the determination of ACFE index. The catalyst sent to the reactor, however, can be either fresh or regenerated or a combination of both. Molecular sieve which may be recirculated to and from the reactor within the reactor apparatus (i.e., via ducts, pipes or annular regions), and which has not been. regenerated or does not contain fresh catalyst, is not to be used in the determination of ACFE index.

In a preferred embodiment of this invention, a feed containing an oxygenate, and optionally a hydrocarbon, either separately or mixed with the oxygenate, is contacted with a catalyst containing a SAPO molecular sieve at process conditions effective to produce olefins in a reactor where the catalyst has an ACFE index of at least about 1.0, preferably at least 1.5. An ACFE index of about 1.0 to 20 is effective, with about 1.5 to about 15 being desirable. An ACFE index of about 2 to about 12 is particularly preferred.

Any standard reactor system can be used, including fixed bed, fluid bed or moving bed systems. Preferred reactors are co-current riser reactors and short contact time, countercurrent free-fall reactors. Desirably, the reactor is one in which an oxygenate feedstock can be contacted with a molecular sieve catalyst at a WHSV of at least about 1 $hr^{-1}$, preferably in the range of from about 1 $hr^{-1}$ to about 1000 $hr^{-1}$, more preferably in the range of from about 20 $hr^{-1}$ to about 1000 $hr^{-1}$, and most preferably in the range of from about 20 $hr^{-1}$ to about 500 $hr^{-1}$. WHSV is defined herein as the weight of oxygenate, and hydrocarbon which may optionally be in the feed, per hour per weight of the molecular sieve content of the catalyst. Because the catalyst or the feedstock may contain other materials which act as inerts or diluents, the WHSV is calculated on the weight basis of the oxygenate feed, and any hydrocarbon which may be present, and the molecular sieve contained in the catalyst.

Preferably, the oxygenate feed is contacted with the rejuvenated catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The process can generally be carried out at a wide range of temperatures. An effective operating temperature range can be from about 200° C. to about 700° C., preferably from about 300° C. to about 600° C., more preferably from about 350° C. to about 550° C. At the lower end of the temperature range, the formation of the desired olefin products may become markedly slow. At the upper end of the temperature range, the process may not form an optimum amount of product.

It is highly desirable to operate at a temperature of at least 300° C. and a Temperature Corrected Normalized Methane Sensitivity (TCNMS) of less than about 0.016. It is particularly preferred that the reaction conditions for making olefin from oxygenate comprise a WHSV of at least about 20 hr$^{-1}$ producing olefins and a TCNMS of less than about 0.016.

As used herein, TCNMS is defined as the Normalized Methane Selectivity (NMS) when the temperature is less than 400° C. The NMS is defined as the methane product yield divided by the ethylene product yield wherein each yield is measured on, or is converted to, a weight % basis. When the temperature is 400° C. or greater, the TCNMS is defined by the following equation, in which T is the average temperature within the reactor in ° C.:

$$TCNMS = \frac{NMS}{1 + (((T - 400)/400) \times 14.84)}$$

The pressure also may vary over a wide range, including autogenous pressures. Effective pressures may be in, but are not necessarily limited to, oxygenate partial pressures at least 1 psia, preferably at least 5 psia. The process is particularly effective at higher oxygenate partial pressures, such as an oxygenate partial pressure of greater than 20 psia. Preferably, the oxygenate partial pressure is at least about 25 psia, more preferably at least about 30 psia. For practical design purposes it is desirable to operate at a methanol partial pressure of not greater than about 500 psia, preferably not greater than about 400 psia, most preferably not greater than about 300 psia.

The conversion of oxygenates to produce light olefins may be carried out in a variety of catalytic reactors. Reactor types include fixed bed reactors, fluid bed reactors, and concurrent riser reactors. Additionally, countercurrent free fall reactors may be used in the conversion process as described in U.S. Pat. No. 4,068,136, the detailed description of which is also expressly incorporated herein by reference.

In a preferred embodiment of the continuous operation, only a portion of the catalyst is removed from the reactor and sent to the regenerator to remove the accumulated coke deposits that result during the catalytic reaction. In the regenerator, the catalyst is contacted with a regeneration medium containing oxygen or other oxidants. Examples of other oxidants include $O_3$, $SO_3$, $N_2O$, NO, $NO_2$, $N_2O_5$, and mixtures thereof It is preferred to supply $O_2$ in the form of air. The air can be diluted with nitrogen, $CO_2$, or flue gas, and steam may be added. Desirably, the $O_2$ concentration in the regenerator is reduced to a controlled level to minimize overheating or the creation of hot spots in the spent or deactivated catalyst. The deactivated catalyst also may be regenerated reductively with $H_2$, CO, mixtures thereof, or other suitable reducing agents. A combination of oxidative regeneration and reductive regeneration can also be employed.

In essence, the coke deposits are removed from the catalyst during the regeneration process, forming a regenerated catalyst. The regenerated catalyst is then returned to the reactor for further contact with feed. Typical regeneration temperatures are in the range of 250° C. to 700° C., desirably in the range of 350° C. to 700° C. Preferably, regeneration is carried out at a temperature range of 450° C. to 70° C.

It is desirable to strip at least some of the volatile organic components which may be adsorbed onto the catalyst or located within its microporous structure prior to entering the regenerator. This can be accomplished by passing a stripping gas over the catalyst in a stripper or stripping chamber, which can be located within the reactor or in a separate vessel. The stripping gas can be any substantially inert medium that is commonly used. Examples of stripping gas are steam, nitrogen, helium, argon, methane, $CO_2$, $CO_2$, flue gas, and hydrogen.

It may be desirable to cool at least a portion of the regenerated catalyst to a lower temperature before it is sent back to the reactor. A heat exchanger located externally to the regenerator may be used to remove some heat from the catalyst after it has been withdrawn from the regenerator. When the regenerated catalyst is cooled, it is desirable to cool it to a temperature which is from about 200° C. higher to about 200° C. lower than the temperature of the catalyst withdrawn from the reactor. More desirably, it is cooled to a temperature from about 10–200° C. lower than the temperature of the catalyst withdrawn from the reactor. This cooled catalyst then may be returned to either some portion of the reactor, the regenerator, or both. When the regenerated catalyst from the regenerator is returned to the reactor, it may be returned to the reactor's catalyst disengaging zone, the reaction zone, and/or the inlet zone. Introducing the cooled catalyst into the reactor or regenerator serves to reduce the average temperature in the reactor or regenerator.

In one embodiment, the reactor and regenerator are configured such that the feed contacts the regenerated catalyst before it is returned to the reactor. In an alternative embodiment, the reactor and regenerator are configured such that the feed contacts the regenerated catalyst after it is returned to the reactor. In yet another embodiment, the feed stream can be split such that feed contacts regenerated catalyst before it is returned to the reactor and after it has been returned to the reactor.

It is preferred the catalyst within the reactor have an average level of coke effective for selectivity to ethylene and/or propylene. Preferably, the average coke level on the catalyst will be from about 2 wt. % to about 30 wt. %, more preferably from about 2 wt. % to about 20 wt. %. In order to maintain this average level of coke on catalyst, the entire volume of catalyst can be partially regenerated under conditions effective to maintain the desired coke content on catalyst. It is preferred, however, to recycle only a portion of the coked catalyst for feed contact without regenerating. This recycle can be performed either internal or external to the reactor. The portion of coked catalyst to be regenerated is preferably regenerated under conditions effective to obtain a regenerated catalyst having a coke content of less than 2 wt. %, preferably less than 1.5 wt. %, and most preferably less than 1.0 wt. %.

In order to make up for any catalyst loss during the regeneration or reaction process, fresh catalyst can be added. Preferably, the fresh catalyst is added to the regenerated catalyst after it is removed from the regenerator, and then both are added to the reactor. However, the fresh catalyst can be added to the reactor independently of the regenerated catalyst. Any amount of fresh catalyst can be added, but it is preferred that an ACFE index of at least 1.5 be maintained.

One skilled in the art will also appreciate that the olefins produced by the oxygenate-to-olefin conversion reaction of the present invention can be polymerized to form polyolefins, particularly polyethylene and polypropylene. The ethylene and propylene can be separated from the oxygenate conversion product by conventional processes. For example, the product stream can be directed to a $C_1$ separation unit, followed by $C_2$ and $C_3$ separation units. The separated $C_2$ and $C_3$ streams can be further separated if desired to give an ethylene and propylene stream containing little ethane and propane, respectively. The separated ethylene and propylene can then be used to make polyethylene and polypropylene.

Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

A preferred polyolefin-forming catalyst is a metallocene catalyst. The preferred temperature range of operation is between 50° C. and 240° C. and the reaction can be carried out at low, medium or high pressure, being anywhere within the range of about 1 bar to 200 bars. For processes carried out in solution, an inert diluent can be used, and the preferred operating pressure range is between 10 bars and 150 bars, with a preferred temperature range of between 120° C. and 230° C. For gas phase processes, it is preferred that the temperature generally be within a range of 60° C. to 160° C., and that the operating pressure be between 5 bars and 50 bars.

In addition to polyolefins, numerous other olefin derivatives may be formed from the olefins recovered therefrom. These include, but are not limited to, aldehydes, alcohols, acetic acid, linear alpha olefins, vinyl acetate, ethylene dichloride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes. The methods of manufacturing these derivatives are well known in the art, and therefore, are not discussed herein.

This invention will be better understood with reference to the following examples, which are intended to illustrate specific embodiments within the overall scope of the invention as claimed.

EXAMPLE 1

A sample of SAPO-34 molecular sieve synthesized with morpholine as the template was heated under nitrogen at 650° C. for 5 hours, followed by heating under dry air at 650° C. for 3 hours, to remove the morpholine template. The sample of SAPO was cooled to 150° C. under dry air. A portion of this sample (0.3 g) was placed in a tubular, fixed bed reactor, to which an on-line GC equipped with a FID and TCD detector was connected for product analysis. This portion of the sample is referred to as "fresh" sample. The remainder of the SAPO-34 sample was placed in an environment with a relative humidity of 90% (saturated $KNO_3$ solution). This portion of the sample is referred to as "aged" sample.

Fresh sample in the reactor was heated under nitrogen for 1 hour at 625° C. (heat up 5° C./min.) prior the introduction of the methanol. The reactor conditions were maintained at 450° C. and 25 psig with a WHSV of 25 $hr^{-1}$. Methanol conversion was calculated as: 100 wt %–(wt % methanol left in product+dimethyl ether left in product). Methanol conversion as a function of the amount of methanol fed/gram of molecular sieve in the reactor is shown in the FIGURE, with the label "fresh" (solid circles).

EXAMPLE 2

A sample of aged (3 days) SAPO-34 molecular sieve was added to a reactor and heated under nitrogen for 1 hour at 625° C. (heat up 5° C./min.) prior to the introduction of methanol. Using the same reaction conditions as in Example 1, methanol conversion was calculated. Methanol conversion as a function of the amount of methanol fed/gram of molecular sieve in the reactor is shown in the FIGURE with the label "3 days aged" (solid triangles).

EXAMPLE 3

A sample of aged (3 days) SAPO-34 molecular sieve was added to a round bottom flask which was connected to a vacuum pump. The sample was evacuated at room temperature to a pressure of about 20 mtorr, while the round bottom was continually rotated. The round bottom flask containing the molecular sieve was cooled with liquid nitrogen while the flask remained under vacuum. After about 30 minutes, the dewer containing the liquid nitrogen was removed, and the sample warmed under a continuous vacuum until a free flowing catalyst was observed in the flask as the flask rotated. Dry air was introduced into the evacuated flask and the flask heated to 150° C. The sample was then transferred to the reactor and evaluated for methanol conversion as in Example 1. Methanol conversion as a function of the amount of methanol fed/gram of molecular sieve in the reactor is shown in the FIGURE with the label "3 days aged+freeze dried" (solid squares).

The FIGURE shows that a SAPO molecular sieve aged for 3 days has almost no catalytic activity. However, a SAPO molecular sieve aged for 3 days and freeze dried exhibited catalytic activity very similar to that of a fresh or non-aged molecular sieve.

Having now fully described this invention, it will be appreciated by those skilled in the art that the invention can be performed within a wide range of parameters within what is claimed, without departing from the spirit and scope of the invention.

What is claimed is:

1. A method for rejuvenating molecular sieve comprising:
    providing molecular sieve having a methanol uptake index of less than 1; and
    freeze drying the molecular sieve until the methanol uptake index is increased by at least 10%.
2. The method of claim 1, wherein the methanol uptake index is increased by at least 50%.

3. The method of claim 2, wherein the methanol uptake index is increased by at least 100%.

4. The method of claim 3, wherein the methanol uptake index is increased by at least 500%.

5. The method of claim 1, wherein the molecular sieve is provided having a methanol uptake index of less than 0.5.

6. The method of claim 1, wherein the molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO44, SAPO-47, SAPO-56, ALPO-5, ALPO-11, ALPO-18, ALPO-31, ALPO-34, ALPO-36, ALPO-37, ALPO-46, the metal containing forms of each thereof, and mixtures thereof.

7. The method of claim 6, wherein the molecular sieve is selected from the group consisting of SAPO-17, SAPO-18, SAPO-34, SAPO-35, SAPO44, SAPO-47, the metal containing forms of each thereof, and mixtures thereof.

8. The method of claim 1, wherein freeze drying is carried out at a pressure of 0.001 mtorr to 700 torr and a temperature of −200° C. to 0° C.

9. A method for rejuvenating molecular sieve containing catalyst comprising:
providing molecular sieve containing catalyst having a methanol uptake index of less than 1; and
freeze drying the molecular sieve containing catalyst until the methanol uptake index is increased by at least 10%.

10. The method of claim 9, wherein the methanol uptake index is increased by at least 50%.

11. The method of claim 10, wherein the methanol uptake index is increased by at least 100%.

12. The method of claim 11, wherein the methanol uptake index is increased by at least 500%.

13. The method of claim 9, wherein the molecular sieve containing catalyst is provided having a methanol uptake index of less than 0.5.

14. The method of claim 9, wherein the molecular sieve in the molecular sieve containing catalyst is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO41, SAPO-42, SAPO-44, SAPO47, SAPO-56, ALPO-5, ALPO-11, ALPO-18, ALPO-31, ALPO-34, ALPO-36, ALPO-37, ALPO-46, the metal containing forms of each thereof, and mixtures thereof.

15. The method of claim 14, wherein the molecular sieve in the molecular sieve containing catalyst is selected from the group consisting of SAPO-17, SAPO-18, SAPO-34, SAPO-35, SAPO44, SAPO-47, the metal containing forms of each thereof, and mixtures thereof.

16. The method of claim 9, wherein freeze drying is carried out at a pressure of 0.001 mtorr to 700 torr and a temperature of −200° C. to 0° C.

* * * * *